United States Patent [19]

Sanderson et al.

[11] Patent Number: 5,185,480
[45] Date of Patent: Feb. 9, 1993

[54] CATALYTIC REMOVAL OF PEROXIDE CONTAMINANTS FROM A METHANOL-TERTIARY BUTYL ALCOHOL RECYCLE STREAM

[75] Inventors: John R. Sanderson, Leander; John F. Knifton, Austin, both of Tex.

[73] Assignee: Texaco Chemical Company, White Plains, N.Y.

[21] Appl. No.: 920,742

[22] Filed: Jul. 28, 1992

[51] Int. Cl.$^5$ ............... C07C 29/88; C07C 27/26
[52] U.S. Cl. ............................ 568/913; 568/914
[58] Field of Search ............ 568/914, 913, 861, 864, 568/910

[56] References Cited

U.S. PATENT DOCUMENTS

| | | | |
|---|---|---|---|
| 4,742,179 | 5/1988 | Sanderson et al. | 568/913 |
| 4,873,380 | 10/1989 | Sanderson et al. | 568/914 |
| 4,912,267 | 3/1990 | Sanderson et al. | 568/914 |
| 5,124,492 | 6/1990 | Jan et al. | 563/914 |

FOREIGN PATENT DOCUMENTS 0215588  3/1987  European Pat. Off. ............ 568/914

Primary Examiner—Werren B. Lone
Attorney, Agent, or Firm—Jack H. Park; Kenneth R. Priem; Carl G. Ries

[57] ABSTRACT

Methanol contaminated with residual amounts of peroxide contaminants such as tertiary butyl hydroperoxide, ditertiary butyl peroxide, allyl tertiary butyl peroxide, etc., can be effectively catalytically treated with a catalyst consisting essentially of titania-supported transition metals to substantially completely decompose the peroxide contaminants to thereby provide a treated methanol product substantially free from contaminating quantities of such peroxides.

13 Claims, 1 Drawing Sheet

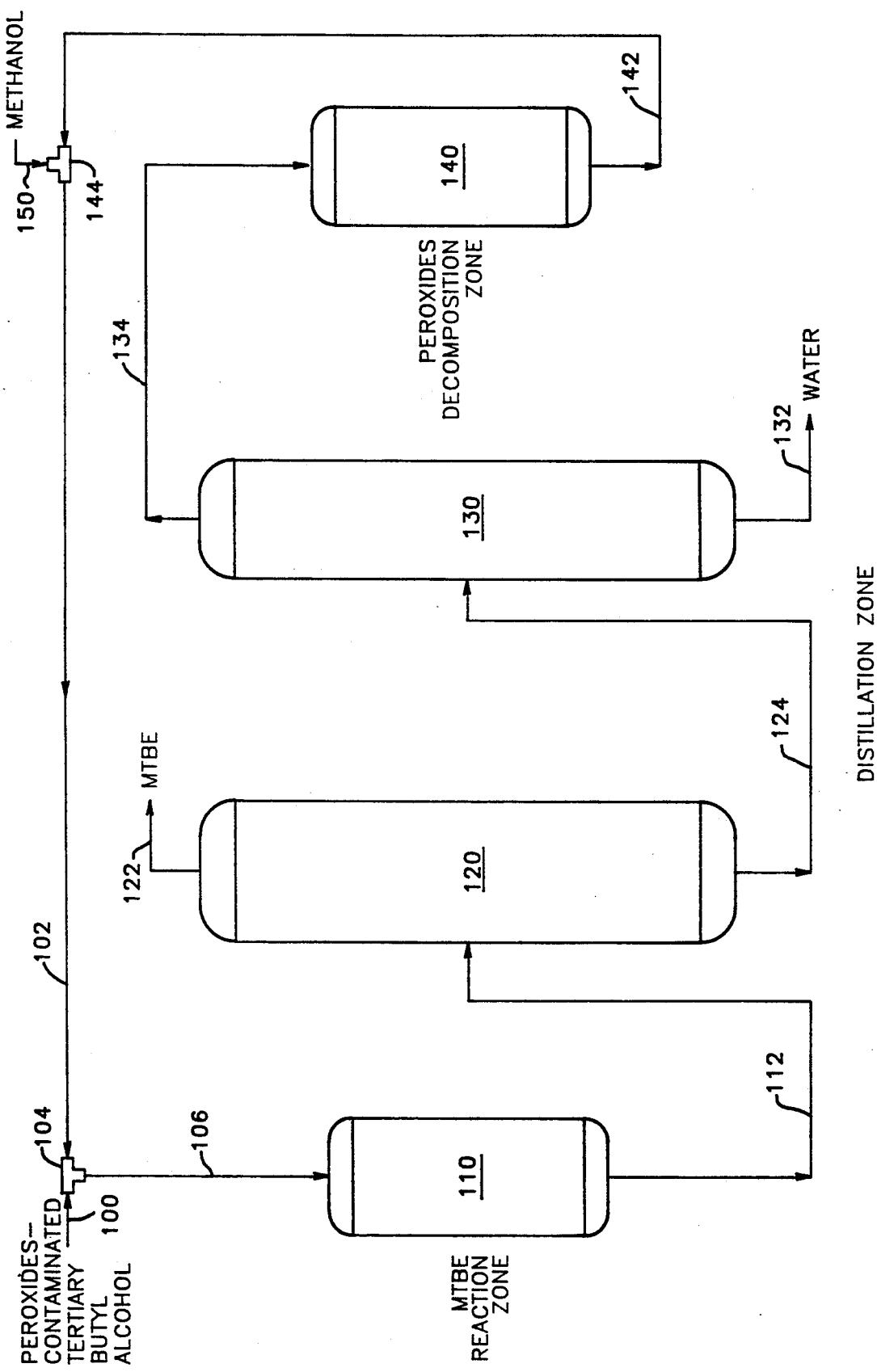

CATALYTIC REMOVAL OF PEROXIDE CONTAMINANTS FROM A METHANOL-TERTIARY BUTYL ALCOHOL RECYCLE STREAM

BACKGROUND OF THE INVENTION

1. Field of the Invention

This invention relates to the catalytic purification of peroxides-contaminated methanol-tertiary butyl alcohol (MeOH/TBA). More particularly, this invention relates to a method for the purification of a MeOH/TBA recycle stream formed during the preparation of methyl tertiary butyl ether (MTBE) from methanol and from tertiary butyl alcohol prepared by the molybdenum-catalyzed reaction of propylene with tertiary butyl hydroperoxide. In accordance with the present invention, methanol contaminated with peroxides is brought into contact with a titanium dioxide (titania) supported transition metal catalyst in order to substantially selectively decompose the peroxide contaminants.

2. Background Information

Methyl tertiary butyl ether (MTBE) can be prepared by the catalytic reaction of tertiary butyl alcohol (TBA) with methanol. Normally, an excess of methanol is used.

Tertiary butyl alcohol can be prepared from isobutane. Isobutane can be reacted with oxygen to form oxygen-containing reaction products, principally tertiary butyl hydroperoxide. The tertiary butyl hydroperoxide can be decomposed (normally in the presence of a catalyst) to form tertiary butyl alcohol. However, the tertiary butyl alcohol will be contaminated with other oxygenated by-products such as tertiary butyl hydroperoxide, ditertiary butyl peroxide, allyl tertiary butyl peroxide, isopropyl hydroperoxide, etc., that are not easily removable by distillation. Tertiary butyl alcohol prepared in this manner can be used as a feedstock for the present invention.

It is known to prepare tertiary butyl alcohol by the molybdenum-catalyzed reaction of propylene with tertiary butyl hydroperoxide. Thus, tertiary butyl hydroperoxide may be reacted with propylene by a process of the type disclosed in Kollar U.S. Pat. No. 3,351,635 to provide a reaction product comprising unreacted propylene, propylene oxide, tertiary butyl alcohol and residual quantities of oxygenated impurities, such as ditertiary butyl peroxide, tertiary butyl hydroperoxide, allyl tertiary butyl peroxide, etc., that remain dissolved in tertiary butyl alcohol recovered from the reaction mixture. Tertiary butyl alcohol prepared in this manner can also be used as a feedstock for the process of the present invention.

Thus peroxide contaminants will be present in the reaction medium that is formed when excess methanol is mixed with the contaminated tertiary butyl alcohol. The contaminants will remain in the MTBE reaction product formed by the catalytic reaction of the contaminated tertiary butyl alcohol with excess methanol to form methyl tertiary butyl ether. When MTBE is prepared in a continuous process by this method, the MTBE reaction product can be separated by distillation into a distillation fraction containing substantially all of the MTBE formed during the reaction and into a separate fraction comprising water, methanol, tertiary butyl alcohol, etc. The separate fraction, after being dewatered, is suitable for use as a recycle fraction.

It has been discovered in accordance with the present invention that when the MeOH/TBA is recovered from the MTBE reaction product for recycle, the peroxide contaminants introduced into the reaction medium with the contaminated tertiary butyl alcohol will be concentrated in the MeOH/TBA recycle stream. As a consequence, the recycle stream will be contaminated with minor quantities of peroxides such as ditertiary butyl peroxide, tertiary butyl hydroperoxide, allyl tertiary butyl peroxide, etc., that need to be removed in order to prevent their accumulation in the reaction medium.

This invention relates to a method for the removal of residual quantities of peroxide contaminants such as ditertiary butyl peroxide, tertiary butyl hydroperoxide, allyl tertiary butyl peroxide, etc., from MeOH/TBA wherein MeOH/TBA contaminated with peroxides is brought into contact with a titanium dioxide (titania) or zirconium oxide supported transition metal catalyst in order to substantially completely decompose the peroxide contaminants.

More particularly, this invention relates to a process for continuously treating a peroxides-contaminated MeOH/TBA stream prior to use of the stream as a recycle stream in the continuous reaction of methanol with tertiary butyl alcohol (TBA) to form methyl tertiary butyl ether wherein MeOH/TBA contaminated with peroxides is brought into contact with a titanium dioxide (titania) supported transition metal catalyst in order to substantially completely decompose the peroxide contaminants.

Still more particularly, this invention relates to a continuous process (a) wherein peroxides-contaminated tertiary butyl alcohol is continuously mixed with excess methanol to form a reaction medium (b) wherein the reaction medium is continuously charged to a reaction zone containing an etherification catalyst to continuously convert a portion of the methanol and tertiary butyl alcohol in the reaction medium into MTBE and water and to form an MTBE reaction product, (c) wherein the MTBE reaction product is continuously separated into an MTBE distillation fraction and a second fraction comprising water, unreacted methanol, unreacted tertiary butyl alcohol and peroxide contaminants, (d) wherein the second fraction is continuously dewatered to form a MeOH/TBA recycle fraction, (e) wherein the MeOH/TBA recycle fraction (which is contaminated with peroxides) is continuously brought into contact with a titanium dioxide (titania) supported transition metal catalyst in order to substantially selectively decompose the peroxide contaminants and (f) wherein the thus-treated MeOH/TBA recycle fraction is continuously mixed with fresh methanol and fresh tertiary butyl alcohol to form a portion of the reaction medium.

When a peroxides-contaminated MeOH/TBA recycle stream is brought into contact with a titania-supported transition metal catalyst of the present invention, the peroxides are decomposed and form tertiary butyl alcohol (main product) and also minor amounts of acetone and methanol. Since the recycle stream already contains tertiary butyl alcohol and methanol, some additional methyl tertiary butyl ether is also formed. A minor amount of isobutylene is also formed by dehydration of the tertiary butyl alcohol present in the recycle stream.

3. Prior Art a. Manufacture of Tertiary Butyl Alcohol

A process for the manufacture of substituted epoxides from alpha olefins such as propylene is disclosed in Kollar U.S. Pat. No. 3,351,653 which teaches that an organic epoxide compound can be made by reacting an olefinically unsaturated compound with an organic hydroperoxide in the presence of a molybdenum, tungsten, titanium, columbium, tantalum, rhenium, selenium, chromium, zirconium, tellurium or uranium catalyst. When the olefin is propylene and the hydroperoxide is tertiary butyl hydroperoxide, propylene oxide and tertiary butyl alcohol are coproducts. U.S. Pat. No. 3,350,422 teaches a similar process using a soluble vanadium catalyst. Molybdenum is the preferred catalyst. A substantial excess of olefin relative to the hydroperoxide is taught as the normal procedure for the reaction. See also U.S. Pat. No. 3,526,645 which teaches the slow addition of organic hydroperoxide to an excess of olefin as preferred.

Stein et al. in U.S. Pat. No. 3,849,451 have improved upon the Kollar process of U.S. Pat. Nos. 3,350,422 and 3,351,635 by requiring a close control of the reaction temperature, between 90°-200° C. and autogenous pressures, among other parameters. Stein et al. also suggests the use of several reaction vessels with a somewhat higher temperature in the last vessel to ensure more complete reaction. The primary benefits are stated to be improved yields and reduced side reactions.

It is known that isobutane can be oxidized with molecular oxygen to form a corresponding tertiary butyl hydroperoxide and that the oxidation reaction can be promoted, for example, with an oxidation catalyst (see Johnston U.S. Pat. No. 3,825,605 and Worrell U.S. Pat. No. 4,296,263).

Thus, tertiary butyl alcohol can be prepared either by the direct thermal or catalytic reduction of tertiary butyl hydroperoxide to tertiary butyl alcohol or by the catalytic reaction of propylene with tertiary butyl hydroperoxide to provide propylene oxide and tertiary butyl alcohol.

It is known that tertiary butyl alcohol can be used as an octane-enhancing component when added to a motor fuel, such as gasoline. Thus, it has heretofore been proposed, as shown, for example, by Grane U.S. Pat. No. 3,474,151 to thermally decompose tertiary butyl hydroperoxide and ditertiary butyl peroxide to form tertiary butyl alcohol. The thermal decomposition must be conducted with care, as pointed out by Grane, in that tertiary butyl alcohol will start to dehydrate at a temperature of about 450° F. and in that the dehydration becomes rapid at temperatures above about 475° F. Moreover, the product from the thermal decomposition normally contains a minor amount of tertiary butyl hydroperoxide and ditertiary butyl peroxide which have an adverse effect upon the quality of motor fuels and must be substantially completely removed if the tertiary butyl alcohol is to be effective. Grane proposes to accomplish this thermally by heating tertiary butyl alcohol containing small quantities of such peroxides at a temperature of 375°-475° F. for a period of 1 to 10 minutes.

This concept was expanded upon by Grane et al. in U.S. Pat. Nos. 4,294,999 and 4,296,262 to provide integrated processes wherein, starting with isobutane, motor-fuel grade tertiary butyl alcohol was prepared by the oxidation of isobutane (e.g., in the presence of a solubilized molybdenum catalyst) to produce a mixture of tertiary butyl alcohol and tertiary butyl hydroperoxide from which a fraction rich in tertiary butyl hydroperoxide could be recovered by distillation. This stream, after being debutanized was subjected to thermal decomposition under pressure at a temperature of less than 300° F. (about 148.8° C.) for several hours to significantly reduce the concentration of the tertiary butyl hydroperoxide. However, the product of this thermal decomposition step still contained residual tertiary butyl hydroperoxide, most of which was thereafter removed by a final thermal treatment of the contaminated tertiary butyl hydroperoxide in the manner taught by Grane U.S. Pat. No. 3,474,151.

Thus, the removal of trace quantities of tertiary butyl hydroperoxide from motor grade tertiary butyl alcohol has received appreciable attention. However, little appears to have been published concerning the removal of trace quantities of ditertiary butyl peroxide, the more refractory of the two peroxides. This may be explainable both because ditertiary butyl peroxide is not always present in trace quantities in motor grade tertiary butyl alcohol (its presence or absence being a function of the reaction conditions used in oxidizing the isobutane starting material) and because, when present, it is present in significantly lower amounts. For example, after decomposition of the major amount of tertiary butyl hydroperoxide formed by the oxidation of isobutane, the tertiary butyl hydroperoxide residual content will normally be about 0.1 to about 1 wt. %, based on the tertiary butyl alcohol, while the residual ditertiary butyl peroxide content, if any, will only be about 0.1 to 0.5 wt. %.

Another refractory peroxide that is frequently present as a contaminant is allyl tertiary butyl peroxide. Allyl tertiary butyl peroxide is more refractory than tertiary butyl hydroperoxide but less refractory that ditertiary butyl peroxide.

b. Manufacture of Methyl Tertiary Butyl Ether

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, Oct. 1984, p. 63; Oil and Gas J., Jan. 1, 1979, p. 76; Chem. Economics Handbook-SRI, Sept. 1986, p. 543-7051P). The cationic ion-exchange resins used in MTBE synthesis normally have the sulfonic acid functionality (see: J. Tejero, J. Mol. Catal., 42 (1987) 257; C. Subramamam et al., Can. J. Chem. Eng., 65 (1987) 613).

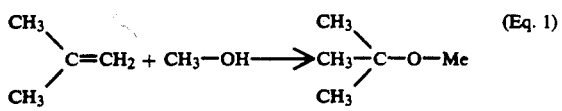

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation. However, as hereafter more fully explained, when tertiary butyl alcohol is prepared by first oxidizing isobutane to form tertiary butyl hydroperoxide and by then thermally or catalytically converting the tertiary butyl hydroperoxide to tertiary butyl alcohol, a number of oxygenation by-products are formed, including ditertiary butyl peroxide and other alkyl peroxides. The oxygenation by-products adversely affect the quality of the tertiary butyl alcohol and methyl tertiary butyl ether made therefrom and are removed only with difficulty.

There is a substantial body of prior art directed to the purification of methyl tertiary butyl ether prepared from isobutylene and methanol. In this situation, the oxygenation by-products are not present in either of the feed materials or in the methyl tertiary butyl ether product.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate plus ethermethanol bottoms, the latter being azeotropically distilled to yield ether-methanol overhead which is recycled to water washing.

The preparation of methyl tert-butyl ether from methyl and tert-butyl alcohols is discussed in S.V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any major problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

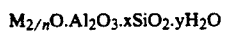

$M_{2/n}O \cdot Al_2O_3 \cdot xSiO_2 \cdot yH_2O$ where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

c. Decomposition of Peroxides

Sanderson et al. U.S. Pat. No. 4,547,598 discloses the use of unsupported cobalt borate and cobalt borate supported on titanium dioxide to decompose organic hydroperoxides to alcohols. It has also been proposed to remove the residual hydroperoxide contaminants from tertiary butyl alcohol through the use of a heterogeneous cobalt oxide catalyst containing a copper oxide promoter as shown, for example, by Coile U.S. Pat. No. 4,059,598. Allison et al. in U.S. Pat. No. 3,505,360 have more generically taught that alkenyl hydroperoxides can be decomposed catalytically through the use of a catalyst based on a metal or compound of a metal of group IV-A, V-A or VI-A.

Other prior art patents relating to the production of hydroperoxides, but not with the problem of residual tertiary hydroperoxide contamination and tertiary butyl alcohol include patents such as Rust U.S. Pat. No. 2,383,919; Harvey U.S. Pat. No. 3,449,217; Poenisch et al. U.S. Pat. No. 3,778,382 and Williams et al. U.S. Pat. No. 3,816,548.

In West German DE 3248465-A a two-step process is disclosed wherein isobutane is oxidized noncatalytically with air to a conversion of about 48–90% to form the corresponding hydroperoxide, which is then catalytically decomposed under hydrogenation conditions in the presence of a supported catalyst such as palladium, platinum, copper, rhenium, ruthenium or nickel to form tertiary butyl alcohol. The decomposition product obtained using 1.3% palladium on lithium spinel as a catalyst contained significant quantities of acetone, water and methanol.

Mabuchi et al. U.S. Pat. No. 4,112,004 discloses a process for preparing monohydric or polyhydric alcohols from organic peroxides in the presence of a nickel catalyst by continuously feeding a solution of the organic peroxide (e.g., butadiene peroxide) and a suspension of the nickel catalyst to a reactor in a controlled ratio and continuously withdrawing reaction mixture at a rate adequate to maintain a constant weight and composition of the reaction mixture in the reactor.

In U.S. Pat. No. 4,123,616 to Mabuchi et al., a process is disclosed for hydrogenating an organic peroxide to the corresponding mono- or polyhydric alcohol in a suspension or fluidized bed process under hydrogen pressure in the presence of a nickel catalyst. Examples are given showing the conversion of butadiene peroxide to 1,4-butane diol and 1,2-butane diol and the conversion of tertiary butyl hydroperoxide to tertiary butyl alcohol.

A process for the decomposition of peroxides, such as a mixture of tertiary butyl hydroperoxide and tertiary butyl alcohol formed by the noncatalyzed oxidation of isobutane is disclosed in Taylor et al. U.S. Pat. No. 4,551,553 wherein the decomposition is catalyzed with a catalytic system composed of chromium and ruthenium which is soluble in the hydroperoxide.

The problems encountered in attempting the thermal removal of contaminating quantities of peroxides such as allyl tertiary butyl peroxide and ditertiary butyl peroxide from tertiary butyl alcohol have led to the provision of a variety of catalytic processes for removing contaminating quantities of peroxides such as allyl tertiary butyl peroxide and ditertiary butyl peroxide from tertiary butyl alcohol as exemplified, for example, by Sanderson et al. U.S. Pat. No. 4,704,482, U.S. Pat. No. 4,705,903, U.S. Pat. No. 4,742,179, U.S. Pat. No. 4,873,390, U.S. Pat. No. 4,910,349, U.S. Pat. No. 4,912,266, U.S. Pat. No. 4,912,267, U.S. Pat. No. 4,922,033, U.S. Pat. No. 4,922,034, U.S. Pat. No. 4,922,035, U.S. Pat. No. 4,922,036, etc.

d. Transition Metal Catalysts

Godfrey U.S. Pat. No. 3,037,025 discloses the preparation of N-alkyl substituted piperazines using catalyst compositions consisting of the metals and oxides of copper, nickel and cobalt (including mixtures thereof) which may also be promoted by the inclusion of a normally non-reducible metal oxide such as chromium, aluminum, iron, calcium, magnesium, manganese and the rare earths. Preferred catalyst compositions are indicated as containing from about 44 to about 74 wt. % of nickel, about 5 to about 55 wt% of copper and about 1 to about 5 wt. % of chromia.

Moss U.S. Pat. No. 3,151,112 discloses catalyst compositions useful for the preparation of morpholines including one or more metals from the group including copper, nickel, cobalt, chromium, molybdenum, manganese, platinum, palladium and rhodium, which may also be promoted with normally nonreducible oxides such as chromium oxide, molybdenum oxide and manganese oxide. Representative catalyst compositions include those containing from about 60 to about 85 wt. % of nickel, about 14 to about 37 wt. % of copper and about 1 to about 5 wt. % of chromia. Nickel, copper, chromia catalysts are also disclosed in Moss U.S. Pat. No. 3,151,115 and Moss U.S. Pat. No. 3,152,998.

Winderl et al. U.S. Pat. No. 3,270,059 teaches the use of catalysts containing a metal of groups I-B and VIII of the Periodic System. Examples of suitable catalysts are stated to be copper, silver, iron, nickel, and particularly, cobalt.

Boettger et al. U.S. Pat. No. 4,014,933 discloses catalysts containing cobalt and nickel promoted with copper such as those containing from about 70 to about 95 wt. % of a mixture of cobalt and nickel and from about 5 to about 30 wt. % of copper.

Habermann U.S. Pat. No. 4,152,353 discloses catalyst compositions comprising nickel, copper and a third component which may be iron, zinc, zirconium or a mixture thereof such as catalysts containing from about 20 to about 49 wt. % of nickel, about 36 to about 79 wt. % of copper and about 1 to about 15 wt. % of iron, zinc, zirconium or a mixture thereof. Similar catalyst compositions are mentioned in Habermann U.S. Pat. No. 4,153,581.

European patent application 0017651 filed Oct. 20, 1980, contains a disclosure of catalyst compositions related to those disclosed by Habermann, such catalyst compositions being composed of nickel or cobalt, copper and iron, and zinc or zirconium such as compositions containing 20 to 90% cobalt, 3 to 72% copper and 1 to 16% of iron, zinc or zirconium and catalyst compositions containing 20 to 49% nickel, 36 to 79% copper and 1 to 16% of iron, zinc or zirconium.

German Offen. 2,721,033 discloses a catalyst composition containing 35% nickel, about 87.5% iron and a minor amount of chromia.

Johansson et al. U.S. Pat. No. 3,766,184 discloses catalyst compositions composed of iron and nickel and/or cobalt.

Sanderson et al. also disclose catalytic methods for the purification of t-butyl alcohol contaminated with residual quantities of tertiary butyl hydroperoxide and ditertiary butyl peroxide using catalysts composed of mixtures of nickel, copper, chromia and iron (U.S. Pat. No. 4,704,482), catalysts composed of mixtures of iron, copper, chromia and cobalt (U.S. Pat. No. 4,705,903), catalysts composed of mixtures of nickel, copper, chromium and barium (U.S. Pat. No. 4,873,380), or catalysts composed of metals selected from group VIB or VIIIB of the Periodic Table (U.S. Pat. No. 4,742,179).

SUMMARY OF THE INVENTION

Tertiary butyl alcohol obtained when propylene is reacted with tertiary butyl hydroperoxide will contain oxygenated impurities including ditertiary butyl peroxide, tertiary butyl hydroperoxide allyl tertiary butyl peroxide, etc., and acetone. Normally, tertiary butyl alcohol prepared in this fashion will contain about 0.1 to about 5 wt. % of ditertiary butyl peroxide, about 0.0 to about 1 wt. % of tertiary butyl hydroperoxide and about 0.05 to about 2.5 wt. % of allyl tertiary butyl peroxide. Minor quantities of other peroxides and other oxygen-containing compounds such as methyl formate, etc., may also be present.

The present invention is directed to a method for the removal of residual quantities of peroxide contaminants such as ditertiary butyl peroxide, tertiary butyl hydroperoxide, allyl tertiary butyl peroxide, etc., from methanol by bringing the contaminated methanol into contact with a titanium dioxide (titania) supported transition metal catalyst in order to substantially selectively decompose the peroxide contaminants.

It has been surprisingly discovered in accordance with the present invention that a MeOH/TBA methanol stream, such as a MeOH/TBA stream that is contaminated with residual quantities of peroxide contaminants including about 0.1 to about 5 wt. % of ditertiary butyl peroxide, about 0.0 to about 1 wt. % of tertiary butyl hydroperoxide and about 0.05 to about 2.5 wt. % of allyl tertiary butyl peroxide, can be effectively treated for the substantially complete removal of such peroxide contaminants by bringing the contaminated MeOH/TBA stream into contact with a titania supported transition metal catalyst under reaction conditions correlated to substantially selectively catalytically decompose the peroxide contaminants to reaction products principally comprising tertiary butyl alcohol and water.

Although the reaction can be conducted batchwise in an autoclave using powdered catalyst, it is preferably conducted on a continuous basis by continuously passing the peroxides-contaminated MeOH/TBA recycle fraction through a reactor containing a fixed bed of a pelleted catalyst of the present invention. The reaction may suitably be conducted at a temperature of about 50° to about 250° C. and a pressure of about 0 to 2000 psig. The reaction is preferably conducted at a temperature within the range of about 80° to about 200° C. and a pressure of about 100 to 800 psig. When the reaction is conducted batchwise, contact time may suitably be from about 0.5 to about 4 hours. When the reaction is conducted on a continuous basis, the peroxides-contaminated MeOH/TBA recycle fraction should be passed over the bed of catalyst at a liquid hourly space velocity of about 0.5 to about 5 volumes of recycle per volume of catalyst per hour.

The specific correlation of conditions to be utilized with any specific catalyst can be determined by one of ordinary skill in the art with comparative ease. Thus, for example, the peroxides-contaminated MeOH/TBA recycle fraction should be analyzed prior to catalytic treatment to determine the level of peroxides contamination. The reaction product can then be analyzed for peroxides content after catalytic treatment. If there is an insufficient reduction of the peroxides, the reaction conditions are not sufficiently severe and should be increased by, for example, increasing reaction temperature or contact time or both. If, on the other hand, there is a significant increase in the level of contamination of by-products such as acetone or methyl formate, the reaction conditions should be ameliorated (e.g., by reducing contact time or reaction temperature or both).

Quite unexpected and surprising is our discovery that one of the more significant reaction products that is formed by the treatment of the peroxides-contaminated MeOH/TBA stream is methyl tertiary butyl ether. Thus, both the quality and quantity of the MeOH/TBA reaction stream are enhanced through the provision of the process of the present invention.

Isobutylene is also formed, but this is not detrimental because when the isobutylene is recycled it will tend to react with methanol to form methyl tertiary butyl ether.

Thus, the process of the present invention is one wherein a MeOH/TBA stream containing contaminating quantities of peroxides is catalytically treated for the decomposition of the peroxides so that they are substantially completely removed and at least partially converted to methyl tertiary butyl ether. This is accomplished without significantly increasing the contamination levels of other undesirable contaminants. The net effect, therefore, is an improvement in the quality of the treated MeOH/TBA recycle stream by the substantially complete removal of peroxide contaminants and by the formation of methyl tertiary butyl ether. This improvement is obtained, in part, because the MeOH/TBA recycle stream contains tertiary butyl alcohol that can react with the methanol to form an additional quantity of methyl tertiary butyl ether.

The process of the present invention is preferably conducted in a continuous manner. The preferred continuous method for the practice of the process of the present invention comprises the steps of:

a. continuously mixing peroxides-contaminated tertiary butyl alcohol with excess methanol, including substantially peroxides-free recycle MeOH/TBA to form a reaction medium;

b. continuously charging the reaction medium to a reaction zone containing a bed of an etherification catalyst to convert a portion of the methanol and tertiary butyl alcohol in the reaction medium into MTBE and water and to form an MTBE etherification reaction product comprising methanol, isobutylene unreacted tertiary butyl alcohol, water, methyl tertiary butyl ether and peroxide contaminants;

c. continuously charging the MTBE etherification reaction product to a first methyl tertiary butyl ether recovery distillation zone and separating it therein into a first lighter distillation fraction comprising isobutylene, methanol and methyl tertiary butyl ether and a second heavier distillation fraction comprising methanol, tertiary butyl alcohol, water and peroxide contaminants;

d. continuously dewatered the second heavier distillation fraction to form a MeOH/TBA recycle fraction (which is contaminated with peroxides);

e. continuously charging the second heavier MeOH/TBA recycle fraction to a peroxides decomposition zone containing a bed of a titania-supported transition metal catalyst under peroxide-decomposition reaction conditions in order to substantially selectively decompose the peroxide contaminants; and f. continuously mixing the thus-treated MeOH/TBA recycle fraction with fresh methanol and fresh tertiary butyl alcohol to form a portion of the reaction medium.

STARTING MATERIALS

The tertiary butyl alcohol feedstock that is used in the practice of the present invention is a peroxides-contaminated tertiary butyl alcohol feedstock, or feed stream, such as a distillation fraction obtained by distillation of a reaction product prepared by the molybdenum catalyzed reaction of propylene with tertiary butyl hydroperoxide to form propylene oxide and tertiary butyl alcohol. Typically, the tertiary butyl alcohol will be contaminated with residual quantities of peroxide contaminants including about 0.1 to about 5 wt. % of ditertiary butyl peroxide, about 0.0 to about 1 wt. % of tertiary butyl hydroperoxide and about 0.05 to about 2.5 wt. % of allyl tertiary butyl peroxide.

The fresh methanol feedstock may suitably comprise a technical grade of methanol.

The tertiary butyl alcohol feedstock and the fresh methanol feedstock are mixed with a substantially peroxides-free MeOH/TBA recycle stream of the type described herein.

The catalyst compositions of the present invention comprise titania or zirconia supported transition metal catalysts, such as one or more of the metals of Group III-B, Group IV-B, Group V-B, Group VI-B, Group VII-B, Group VIII-B and Group I-B. More preferably, the catalyst will consist essentially of about 85 to about 99.9 wt. % of titania or zirconia and about 15 to about 0.1 wt. % of transition metal catalyst. A preferred group of titania-supported catalysts are catalysts of the type disclosed in Moss U.S. Pat. No. 3,151,112 which consists essentially of one or more of the metals from the group consisting of copper, nickel, cobalt, chromium, aluminum, iron, calcium, magnesium, and manganese. The catalyst will preferably consist essentially of a mixture of a hydrogen-reducible transition metal with a normally non-reducible transition metal oxide such as chromium oxide, molybdenum oxide or manganese oxide. An example of a preferred catalyst is a nickel, copper, chromia catalyst of the type disclosed in Moss U.S. Pat. No. 3,151,112 consisting essentially of a mixture of about 60 to about 85 wt. % of nickel and about 14 to about 37 wt. % of copper with about 1 to about 5 wt. % of chromia supported on titania. Another example of a suitable catalyst is a catalyst of the type disclosed in Sanderson et al. U.S. Pat. No. 4,705,903 consisting essentially, on an oxygen-free basis, of about 20 to 80 wt. % of iron, about 5 to about 40 wt. % of copper, about 0.1 to about 10 wt. % of chromium and about 0.01 to about 5 wt. % of cobalt.

BRIEF DESCRIPTION OF THE DRAWING

The drawing is a schematic flow sheet with conventional parts omitted showing the general sequence that is used in accordance with the present invention in purifying the methanol recycle stream.

In the drawing, for convenience, conventional parts such as heat exchangers, reflux condensers, reboilers, valves, pumps, sensors, flow control regulation apparatus, etc., have been omitted.

DESCRIPTION OF THE PREFERRED EMBODIMENT

Turning now to the drawing, there is shown a schematic flow sheet illustrating a preferred method for practicing the process of the present invention.

In accordance with the preferred embodiment of the present invention, peroxides-contaminated tertiary butyl alcohol from a suitable source (not shown) is charged by a charge line 100 to a junction 104 where it is mixed with a molar excess of substantially peroxides-free methanol (e.g., from 2 to 5 moles of methanol per mole of tertiary butyl alcohol) charged by a feed line 102 leading from a junction 144 and composed of fresh methanol charged to junction 144 by a line 150 and recycle methanol obtained in a manner to be described which is charged to the junction 144 by a line 142.

The reaction medium formed in the junction 104 by the mixing of the peroxides-contaminated tertiary butyl alcohol 100 with the excess methanol 102 is routed by a charge line 106 to an MTBE reaction zone containing a bed of suitable catalyst (not shown).

The reaction medium 106 may be charged to the reaction zone 110 at a suitable charge rate, for example being charged at a liquid hourly space velocity of about 0.5 to about 5 volumes of reaction medium per volume of catalyst per hour. The reaction may be conducted at a temperature of about 50° to about 250° C. and a pressure of about 0 to 2000 psig. and more preferably at a temperature within the range of about 80° to about 200° C. and a pressure of about 100 to 800 psig. As a consequence, a significant portion (e.g., 0.5 to about 3 wt. %) of the tertiary butyl alcohol will react with the methanol to form MTBE. The resultant MTBE reaction product is discharged from the MTBE reaction zone 110 by a line 112 leading to a distillation zone of any suitable construction.

In accordance with the illustrated embodiment the distillation zone comprises distillation columns 120 and 130 operating in series. Thus, the MTBE reaction product 112 is charged to the first distillation column 110 where it is separated into a lighter fraction comprising substantially all of the MTBE formed in the reaction zone 110 and lesser amounts of other components such as methanol and tertiary butyl alcohol. A heavier distillation fraction is discharged from the distillation column 120 by a feed line 124 leading to a second distillation column 130 wherein the heavier distillation fraction 124 is separated into a lighter MeOH/TBA recycle fraction 134 and a heavier water fraction 132 whereby water of reaction is discharged from the system.

The peroxide impurities such as tertiary butyl hydroperoxide, ditertiary butyl peroxide, allyl tertiary butyl peroxide, isopropyl hydroperoxide, etc., introduced into the system with the contaminated tertiary butyl alcohol feedstock 100 will pass without significant change through the MTBE reaction zone 110, the first distillation column 120 and the second distillation column 130 and will be concentrated in the MeOH/TBA recycle fraction 134. Thus, typically, the MeOH/TBA recycle stream 134 will contain from about 45 to about 55 wt. % of methanol, from about 30 to about 40 wt. % of tertiary butyl alcohol, about 5 to 15 wt. % of water, from about 0 to about 5 wt. % of methyl tertiary butyl ether and from about 0.1 to about 5 wt. % of peroxide impurities, such as, for example, about 0.1 to about 5 wt. % of ditertiary butyl peroxide, about 0.0 to about 1 wt. % of tertiary butyl hydroperoxide, about 0.05 to about 2.5 wt. % of allyl tertiary butyl peroxide, etc., including small amounts of other peroxides and other oxygen-containing impurities such as methyl formate, acetone, etc.

In accordance with the present invention, the peroxides-contaminated MeOH/TBA stream 134 is charged to a peroxide decomposition zone 140 containing a fixed bed of a pelleted titania-supported transition metal catalyst, such as, for example, a titania-supported iron, copper, chromia catalyst having the following composition: iron=0.25%, chromium=0.06%, copper=0.01%. The peroxides-contaminated methanol recycle fraction 134 is brought into contact with the pelleted titania-supported nickel, copper, chromia catalyst in the peroxides decomposition zone 140 under appropriate reaction conditions, for example being charged at a liquid hourly space velocity of about 0.5 to about 5 volumes of methanol recycle fraction per volume of catalyst per hour. The reaction may be conducted at a temperature of about 50° to about 250° C. and a pressure of about 0 to 2000 psig. and more preferably at a temperature within the range of about 80° to about 200° C. and a pressure of about 100 to 800 psig. As a consequence, the peroxides charged to the peroxide decomposition zone 140 will be substantially completely decomposed into decomposition products such as tertiary butyl alcohol and water. Minor amounts of other contaminants such as acetone, methyl formate, isobutylene, etc., will also be formed. At least a portion of the tertiary butyl alcohol and the isobutylene formed in the peroxides decomposition zone 140 will react with methanol present in the methanol recycle stream to form MTBE.

As a consequence, the MeOH/TBA recycle fraction discharged from the peroxides decomposition zone 142 will comprise about 45 to about 55 wt. % of methanol, from about 30 to about 40 wt. % of tertiary butyl alcohol, about 5 to 15 wt. % of water, from about 0 to about 5 wt. % of methyl tertiary butyl ether and other oxygen-containing impurities such as methyl formate, acetone, etc. The MeOH/TBA recycle fraction 142 is charged to the junction 144 where it is mixed with fresh methanol 150 to form a methanol mixture that is discharged from the junction 144 by a methanol feed line 102 leading to the junction 104.

WORKING EXAMPLES

A. REACTOR

The reactor was a stainless steel tube (0.51"×29") which was electrically heated. Liquid feed was pumped into the bottom of the reactor. Pressure was regulated with a Skinner Uni-Flow valve and a Foxboro controller. The liquid feed was pumped with a Ruska dual drive pump.

B. FEED

The feed was a blend of 10 wt. % of water, 51 wt. % of methanol, 35 wt. % of tertiary butyl alcohol, 1.0 wt. % of methyl tertiary butyl ether and 2.5 wt. % of ditertiary butyl peroxide.

C. CATALYST PREPARATION (6773-14)

Iron (III) acetylacetonate (5 g), chromium (III) acetylacetonate (5 g), and copper (II) acetylacetonate were dissolved in 500 ml acetone and added to 500 g titania pellets (⅛"). This was let stand for 1.0 hour with occasional stirring and then the acetone was removed on a rotary evaporator. The pellets were then calcined in air at 400° C. overnight, followed by reduction with hydrogen at 200° C. for 3 hours.

% Fe=0.25, % Cr=0.06, % Cu=0.01

D. CATALYST PREPARATION (6773-15)

Cobalt (III) acetylacetonate (5 g), manganese (III) acetylacetonate (5 g) were dissolved in 500 ml acetone and added to 500 g titania pellets (⅛"). The pellets were let stand for 1 hour with occasional stirring and then the acetone removed on a rotary evaporator. The pellets were then calcined in air at 400° C. overnight, followed by reduction with hydrogen at 200° C. for 3 hours.

% cobalt=0.16, % Mn=0.05

E. DECOMPOSITION

Data on the catalytic decomposition of the ditertiary butyl peroxide was generated in a plurality of runs conducted in the reactor under reaction conditions including a pressure of 500 psig, feed rates of from 100 to 400 cc/hr, temperatures ranging from 120 to 180° C., run lengths of 4 hours and space velocities of from 1 to 4 cc of feed per hour per cc of catalyst. The data are shown in the following tables.

TABLE I

| Catalytic Decomposition of DTBP in a Continuous Reactor | | | | | |
|---|---|---|---|---|---|
| Notebook Number | 6773-16-L | 6773-38-1 | 6773-38-2 | 6773-38-3 | 6773-38-4 |
| Catalyst |  | Fe, Cu, Cr on TiO2 | Fe, Cu, Cr on TiO2 | Fe, Cu, Cr on TiO2 | Fe, Cu, Cr on TiO2 |
| Reactor (cc) |  | 100 | 100 | 100 | 100 |
| Pressure (psig) |  | 500 | 500 | 500 | 500 |
| Feed Rate (cc/hr) |  | 100 | 100 | 100 | 100 |
| Temperature (°C.) |  | 120 | 140 | 160 | 180 |
| Time on Stream (hr) |  | 4 | 4 | 4 | 4 |
| Space Vel. (cc/cc) |  | 1.0 | 1.0 | 1.0 | 1.0 |
| DTBP Conversion (%) |  | 12.3 | 37.9 | 88.3 | 100.0 |
| TBA Conversion (%) |  | 0.3 | 0.0 | 0.0 | 0.0 |
| Remarks | H2O Free Basis | H2O Free Basis | H2O Free Basis | H2O Free Basis | H2O Free Basis |
| Composition: | | | | | |
| IC4 | 0.004 | 0.011 | 0.007 | 0.013 | 0.223 |
| MEOH/MF | 55.398 | 55.922 | 55.760 | 55.725 | 55.772 |
| Acetone | 0.009 | 0.053 | 0.260 | 0.759 | 0.993 |
| MTBE | 1.248 | 1.236 | 1.197 | 1.273 | 1.951 |
| TBA | 39.997 | 39.889 | 40.706 | 41.533 | 40.576 |
| DTBP | 2.960 | 2.597 | 1.839 | 0.347 | 0.000 |
| TBHP | 0.000 | 0.000 | 0.000 | 0.001 | 0.021 |

TABLE II

| Catalytic Decomposition of DTBP in a Continuous Reactor | | | | | |
|---|---|---|---|---|---|
| Notebook Number | 6773-16-L | 6773-39-1 | 6773-39-2 | 6773-39-3 | 6773-39-4 |
| Catalyst |  | Fe, Cu, Cr on TiO2 | Fe, Cu, Cr on TiO2 | Fe, Cu, Cr on TiO2 | Fe, Cu, Cr on TiO2 |
| Reactor (cc) |  | 100 | 100 | 100 | 100 |
| Pressure (psig) |  | 500 | 500 | 500 | 500 |
| Feed Rate (cc/hr) |  | 200 | 200 | 200 | 200 |
| Temperature (°C.) |  | 120 | 140 | 160 | 180 |
| Time on Stream (hr) |  | 4 | 4 | 4 | 4 |
| Space Vel. (cc/cc) |  | 2.0 | 2.0 | 2.0 | 2.0 |
| DTBP Conversion (%) |  | 10.6 | 29.4 | 73.3 | 98.1 |
| TBA Conversion (%) |  | 0.0 | 0.0 | 0.0 | 0.0 |
| Remarks | H2O Free Basis | H2O Free Basis | H2O Free Basis | H2O Free Basis | H2O Free Basis |
| Composition: | | | | | |
| IC4 | 0.004 | 0.004 | 0.009 | 0.012 | 0.045 |
| MEOH/MF | 55.398 | 55.855 | 55.875 | 55.683 | 55.728 |
| Acetone | 0.009 | 0.037 | 0.204 | 0.705 | 1.098 |
| MTBE | 1.248 | 1.183 | 1.224 | 1.221 | 1.372 |
| TBA | 39.997 | 40.046 | 40.334 | 41.274 | 41.315 |
| DTBP | 2.960 | 2.646 | 2.091 | 0.789 | 0.057 |
| TBHP | 0.000 | 0.000 | 0.000 | 0.000 | 0.015 |

TABLE III

| Catalytic Decomposition of DTBP in a Continuous Reactor | | | | | |
|---|---|---|---|---|---|
| Notebook Number | 6773-16-M | 6773-40-1 | 6773-40-2 | 6773-40-3 | 6773-40-4 |
| Catalyst |  | Fe, Cu, Cr | Fe, Cu, Cr | Fe, Cu, Cr | Fe, Cu, Cr |

TABLE III-continued

Catalytic Decomposition of DTBP in a Continuous Reactor

| Notebook Number | 6773-16-M | 6773-40-1 | 6773-40-2 | 6773-40-3 | 6773-40-4 |
|---|---|---|---|---|---|
| | | on TiO2 | on TiO2 | on TiO2 | on TiO2 |
| Reactor (cc) | | 100 | 100 | 100 | 100 |
| Pressure (psig) | | 500 | 500 | 500 | 500 |
| Feed Rate (cc/hr) | | 400 | 400 | 400 | 400 |
| Temperature (°C.) | | 120 | 140 | 160 | 180 |
| Time on Stream (hr) | | 4 | 4 | 4 | 4 |
| Space Vel. (cc/cc) | | 4.0 | 4.0 | 4.0 | 4.0 |
| DTBP Conversion (%) | | 1.2 | 10.8 | 43.2 | 88.7 |
| TBA Conversion (%) | | 2.3 | 1.4 | 0.3 | 0.0 |
| Remarks | H2O Free Basis | H2O Free Basis | H2O Free Basis | H2O Free Basis | H2O Free Basis |
| Composition: | | | | | |
| IC4 | 0.003 | 0.001 | 0.003 | 0.005 | 0.011 |
| MEOH/MF | 54.786 | 55.917 | 55.829 | 55.813 | 55.719 |
| Acetone | 0.009 | 0.015 | 0.087 | 0.434 | 1.028 |
| MTBE | 1.225 | 1.185 | 1.156 | 1.207 | 1.242 |
| TBA | 40.795 | 39.876 | 40.215 | 40.664 | 41.273 |
| DTBP | 2.789 | 2.756 | 2.488 | 1.584 | 0.315 |
| TBHP | 0.000 | 0.000 | 0.000 | 0.000 | 0.000 |

TABLE IV

Catalytic Decomposition of DTBP in a Continuous Reactor

| Notebook Number | 6773-16-O | 6773-59-1 | 6773-59-2 | 6773-59-3 | 6773-59-4 |
|---|---|---|---|---|---|
| Catalyst | | Co, Mn on TiO2 | Co, Mn on TiO2 | Co, Mn on TiO2 | Co, Mn on TiO2 |
| Reactor (cc) | | 100 | 100 | 100 | 100 |
| Pressure (psig) | | 500 | 500 | 500 | 500 |
| Feed Rate (cc/hr) | | 200 | 200 | 200 | 200 |
| Temperature (°C.) | | 120 | 140 | 160 | 180 |
| Time on Stream (hr) | | 4 | 4 | 4 | 4 |
| Space Vel. (cc/cc) | | 2.0 | 2.0 | 2.0 | 2.0 |
| DTBP Conversion (%) | | 0.0 | 35.5 | 87.5 | 99.8 |
| TBA Conversion (%) | | 2.9 | 0.0 | 0.0 | 0.0 |
| Remarks | H2O Free Basis | H2O Free Basis | H2O Free Basis | H2O Free Basis | H2O Free Basis |
| Composition: | | | | | |
| IC4 | 0.004 | 0.002 | 0.003 | 0.005 | 0.021 |
| MEOH/MF | 56.015 | 56.538 | 55.610 | 55.231 | 55.273 |
| Acetone | 0.008 | 0.053 | 0.397 | 1.356 | 1.524 |
| MTBE | 1.194 | 1.397 | 1.208 | 1.204 | 1.239 |
| TBA | 39.912 | 38.745 | 40.478 | 41.140 | 41.149 |
| DTBP | 2.792 | 2.862 | 1.800 | 0.348 | 0.005 |
| TBHP | 0.000 | 0.000 | 0.000 | 0.000 | 0.000 |

TABLE IV

Catalytic Decomposition of DTBP in a Continuous Reactor

| Notebook Number | 6773-16-O | 6773-60-1 | 6773-60-2 | 6773-60-3 | 6773-60-4 |
|---|---|---|---|---|---|
| Catalyst | | Co, Mn on TiO2 | Co, Mn on TiO2 | Co, Mn on TiO2 | Co, Mn on TiO2 |
| Reactor (cc) | | 100 | 100 | 100 | 100 |
| Pressure (psig) | | 500 | 500 | 500 | 600 |
| Feed Rate (cc/hr) | | 400 | 400 | 400 | 400 |
| Temperature (°C.) | | 120 | 140 | 160 | 180 |
| Tims on stream (hr) | | 4 | 4 | 4 | 4 |
| Space Vel. (cc/cc) | | 4.0 | 4.0 | 4.0 | 4.0 |
| DTBP Conversion (%) | | 3.8 | 10.4 | 58.5 | 97.9 |
| TBA Conversion (%) | | 0.1 | 0.0 | 0.0 | 0.0 |
| Remarks | H2O Free Basis | H2O Free Basis | H2O Free Basis | H2O Free Basis | H2O Free Basis |
| Composition: | | | | | |
| IC4 | 0.004 | 0.002 | 0.005 | 0.005 | 0.008 |
| MEOH/MF | 56.015 | 55.747 | 55.870 | 55.770 | 55.582 |
| Acetone | 0.008 | 0.037 | 0.133 | 0.687 | 1.337 |
| MTBE | 1.194 | 1.221 | 1.217 | 1.180 | 1.205 |
| TBA | 39.912 | 39.890 | 40.087 | 41.019 | 41.459 |
| DTBP | 2.792 | 2.687 | 2.502 | 1.158 | 0.058 |
| TBHP | 0.000 | 0.000 | 0.000 | 0.000 | 0.004 |

TABLE VI

Catalytic Decomposition of DTBP in a Continuous Reactor

| Notebook Number | 6773-16-O | 6773-55-1 | 6773-55-2 | 6773-55-3 | 6773-55-4 |
|---|---|---|---|---|---|
| Catalyst | | Glass Beads | Glass Beads | Glass Beads | Glass Beads |
| Reactor (cc) | | 100 | 100 | 100 | 100 |
| Pressure (psig) | | 500 | 500 | 500 | 500 |
| Feed Rate (cc/hr) | | 100 | 100 | 100 | 100 |
| Temperature (°C.) | | 130 | 140 | 150 | 160 |
| Time on Stream (hr) | | 4 | 4 | 4 | 4 |
| Space Vel. (cc/cc) | | 1.0 | 1.0 | 1.0 | 1.0 |
| DTBP Conversion (%) | | 0.0 | 6.2 | 65.4 | 97.5 |
| TBA Conversion (%) | | 3.7 | 4.6 | 2.2 | 0.0 |
| Remarks | H2O Free Basis | H2O Free Basis | H2O Free Basis | H2O Free Basis | H2O Free Basis |
| Composition: | | | | | |
| IC4 | 0.004 | 0.001 | 0.001 | 0.002 | 0.004 |
| MEOH/MF | 56.015 | 56.892 | 57.297 | 57.033 | 56.040 |
| Acetone | 0.008 | 0.000 | 0.112 | 0.863 | 1.113 |
| MTBE | 1.194 | 1.447 | 1.493 | 1.509 | 1.288 |
| TBA | 39.912 | 38.431 | 38.094 | 39.029 | 40.763 |
| DTBP | 2.792 | 2.805 | 2.619 | 0.965 | 0.069 |
| TBHP | 0.000 | 0.000 | 0.000 | 0.000 | 0.001 |

TABLE VII

Catalytic Decomposition of DTBP in a Continuous Reactor

| Notebook Number | 6773-16-O | 6773-56-1 | 6773-56-2 | 6773-56-3 | 6773-56-4 |
|---|---|---|---|---|---|
| Catalyst | | Glass Beads | Glass Beads | Glass Beads | Glass Beads |
| Reactor (cc) | | 100 | 100 | 100 | 100 |
| Pressure (psig) | | 500 | 500 | 500 | 500 |
| Feed Rate (cc/hr) | | 200 | 200 | 200 | 200 |
| Temperature (°C.) | | 130 | 140 | 150 | 160 |
| Time on stream (hr) | | 4 | 4 | 4 | 4 |
| Space Vel. (cc/cc) | | 2.0 | 2.0 | 2.0 | 2.0 |
| DTBP conversion (%) | | 8.0 | 19.7 | 29.9 | 56.0 |
| TBA Conversion (%) | | 0.0 | 0.0 | 0.0 | 0.0 |
| Remarks | H2O Free Basis | H2O Free Basis | H2O Free Basis | H2O Free Basis | H2O Free Basis |
| Composition: | | | | | |
| IC4 | 0.004 | 0.003 | 0.003 | 0.004 | 0.002 |
| MEOH/MF | 56.015 | 55.721 | 54.801 | 55.050 | 55.409 |
| Acetone | 0.008 | 0.076 | 0.150 | 1.050 | 0.734 |
| MTBE | 1.194 | 1.260 | 1.167 | 1.217 | 1.228 |
| TBA | 39.912 | 39.977 | 41.212 | 40.266 | 40.825 |
| DTBP | 2.792 | 2.570 | 2.243 | 1.956 | 1.229 |
| TBHP | 0.000 | 0.000 | 0.000 | 0.000 | 0.000 |

TABLE VIII

Catalytic Decomposition of DTBP in a Continuous Reactor

| Notebook Number | 6773-16-O | 6773-57-1 | 6773-57-2 | 6773-57-3 | 6773-57-4 |
|---|---|---|---|---|---|
| Catalyst | | Glass Beads | Glass Beads | Glass Beads | Glass Beads |
| Reactor (cc) | | 100 | 100 | 100 | 100 |
| Pressure (psig) | | 500 | 500 | 500 | 500 |
| Feed Rate (cc/hr) | | 400 | 400 | 400 | 400 |
| Temperature (°C.) | | 130 | 140 | 150 | 160 |
| Time on Stream (hr) | | 4 | 4 | 4 | 4 |
| Space Vel. (cc/cc) | | 4.0 | 4.0 | 4.0 | 4.0 |
| DTBP Conversion (%) | | 6.6 | 5.8 | 15.3 | 34.2 |
| TBA Conversion (%) | | 0.0 | 0.0 | 0.0 | 0.0 |
| Remarks | H2O Free Basis | H2O Free Basis | H2O Free Basis | H2O Free Basis | H2O Free Basis |
| Composition: | | | | | |
| IC4 | 0.004 | 0.002 | 0.003 | 0.002 | 0.002 |
| MEOH/MF | 56.015 | 55.476 | 55.726 | 55.703 | 55.661 |
| Acetone | 0.008 | 0.025 | 0.058 | 0.131 | 0.371 |
| MTBE | 1.194 | 1.209 | 1.260 | 1.211 | 1.221 |
| TBA | 39.912 | 40.295 | 39.939 | 40.278 | 40.548 |
| DTBP | 2.792 | 2.608 | 2.631 | 2.365 | 1.837 |
| TBHP | 0.000 | 0.000 | 0.000 | 0.000 | 0.000 |

The foregoing examples have been given by way of illustration and are not intended as limitations on the scope of this invention, as defined by the appended claims.

Having thus described our invention, what is claimed is:

1. A method for enhancing the quality of a methanol/tertiary butyl alcohol (MeOH/TBA) recycle stream contaminated with peroxides including ditertiary butyl peroxide, tertiary butyl hydroperoxide and allyl tertiary butyl peroxide, which comprises the steps of:
   a. continuously contacting said contaminated MeOH/TBA in a peroxide decomposition reaction zone with a peroxide decomposition catalyst at a temperature of about 50° to about 250° C. at a pressure of about 0 to 2,000 psig for a period of time sufficient to substantially decompose said peroxide contaminants, and
   b. recovering from the products of said reaction a MeOH/TBA product contaminated with not more than about 300 ppm of peroxide contaminants,
   c. said catalyst consisting essentially of a titania supported transition metal.

2. A method as in claim 1 wherein the catalyst consists essentially of a mixture of iron, copper and chromia supported on titania.

3. A method as in claim 1 wherein the catalyst consists essentially of a mixture of cobalt and manganese supported on titania.

4. A method as in claim wherein the catalyst is calcined in air at 200°–600° C. and subsequently partially reduced in a stream of hydrogen at 100–500° C.

5. A method for enhancing the quality of a MeOH/TBA feedstock contaminated with peroxides including about 0.1 to about 5 wt. % of ditertiary butyl peroxide, about 0.0 to about 1 wt. % of tertiary butyl hydroperoxide and about 0.05 to about 2.5 wt. % of allyl tertiary butyl peroxide, which comprises:
   a. continuously contacting said MeOH/TBA contaminated feedstock in a peroxide decomposition reaction zone with a peroxide decomposition catalyst at a temperature within the range of about 80° to about 200° C., a pressure of about 100 to about 800 psig and a space velocity of about 0.5 to about 5 volumes of contaminated MeOH/TBA feedstock per hour per volume of catalyst to substantially decompose said peroxide contaminants, and
   b. recovering from the products of said reaction a MeOH/TBA product contaminated with not more than about 300 ppm of peroxide contaminants,
   c. said catalyst consisting essentially of a titania-supported transition metal.

6. A method as in claim 5 wherein the catalyst consists essentially of a mixture of about 0.1 to about 15 wt. % of iron, about 0.01 to about 2.5 wt. % of copper and about 0.01 to about 5.0 wt. % of chromia supported on titania.

7. A method as in claim 5 wherein the catalyst consists essentially of a mixture of cobalt and manganese supported on titania.

8. A method which comprises the steps of:
   a. mixing a peroxides-contaminated tertiary butyl alcohol feedstock with a peroxides-free methanol feedstock to form a reaction medium,
   b. charging said reaction medium to an etherification reaction zone containing a bed of an etherification catalyst to convert a portion of said tertiary butyl alcohol and said methanol to methyl tertiary butyl ether and to form a methyl tertiary butyl ether reaction product,
   c. charging said methyl tertiary butyl ether reaction product, to a distillation zone and separating it therein into a methyl tertiary butyl ether distillation fraction, a peroxides-contaminated MeOH/TBA recycle fraction and a water fraction,
   d. charging said peroxides-contaminated MeOH/TBA recycle fraction to a peroxides-decomposition zone containing a bed of a peroxides decomposition catalyst under reaction conditions correlated for the substantially complete decomposition of said peroxides to thereby form a substantially peroxides-free MeOH/TBA recycle fraction, and
   e. recycling said substantially peroxides-free MeOH/TBA recycle fraction to said etherification reaction zone,
   f. said peroxides decomposition catalyst consisting essentially of a mixture of transition metals supported on titania.

9. A method as in claim 8 wherein the catalyst consists essentially of a mixture of about 0.1 to about 15 wt. % of iron, about 0.01 to about 25 wt. % of copper and about 0.01 to about 5.0 wt. % of chromia supported on titania.

10. A method as in claim 8 wherein the catalyst consists essentially of a mixture of cobalt and manganese supported on titania.

11. A method which comprises the steps of:
   a. mixing a peroxides-contaminated tertiary butyl alcohol feedstock with a peroxides-free methanol feedstock to form a reaction medium,
   b. said peroxides-contaminated tertiary butyl alcohol containing about 0.1 to about 5 wt. % of ditertiary butyl peroxide, about 0.0 to about 1 wt. % of tertiary butyl hydroperoxide, about 0.05 to about 2.5 wt. % of allyl tertiary butyl peroxide, and minor quantities of other peroxides and other oxygen-containing compounds including methyl formate,
   c. charging said reaction medium to an etherification reaction zone containing a bed of an etherification catalyst and establishing etherification reaction conditions therein including a temperature within the range of about 80° to 200° C., a pressure of about 100 to about 800 psig and a space velocity of about 0.5 to 5 volumes of said reaction medium per volume of etherification catalyst per hour to convert a portion of said tertiary butyl alcohol and said methanol to methyl tertiary butyl ether and to form a peroxides-contaminated methyl tertiary butyl ether reaction product,
   d. charging said methyl tertiary butyl ether reaction product to a distillation zone and separating it therein into a methyl tertiary butyl ether distillation fraction, a peroxides-contaminated MeOH/TBA recycle fraction and a water fraction,
   e. said MeOH/TBA recycle fraction discharged from the peroxides decomposition zone comprising from about 45 to about 55 wt. % of methanol, from about 30 to about 40 wt. % of tertiary butyl alcohol, about 5 to 15 wt. % of water, from about 0 to about 5 wt. % of methyl tertiary butyl ether and other oxygen-containing impurities including methyl formate and acetone,
   f. charging said peroxides-contaminated MeOH/TBA recycle fraction to a peroxides-decomposition zone containing a bed of a peroxides decomposition catalyst under reaction conditions correlated for the substantially complete decomposition of said peroxides including a temperature within the range of about 80° to 200° C., a pressure of about 100 to about 800 psig and a space velocity of about 0.5 to 5 volumes of said reaction medium per volume of peroxides-decomposition catalyst per hour to thereby form a substantially peroxides-free MeOH/TBA recycle fraction, and g. recycling said substantially peroxides-free MeOH/TBA recycle fraction to said etherification reaction zone, h. said peroxides decomposition catalyst consisting essentially of a mixture of transition metals supported on titania.

12. A method as in claim 11 wherein the catalyst consists essentially of a mixture of about 0.1 to about 15 wt. % of iron, about 0.01 to about 25 wt. % of copper and about 0.01 to about 5.0 wt. % of chromia supported on titania.

13. A method as in claim 11 wherein the catalyst consists essentially of a mixture of cobalt and manganese supported on titania.

* * * * *